(12) United States Patent
Khan

(10) Patent No.: US 8,906,390 B2
(45) Date of Patent: Dec. 9, 2014

(54) SYNTHETIC LIPID RAFTS AND METHODS OF USE

(75) Inventor: Shaharyar Khan, Charlottesville, VA (US)

(73) Assignee: Gencia Corporation, Charlottsville, VA (US)

(*) Notice: Subject to any disclaimer, the term of this patent is extended or adjusted under 35 U.S.C. 154(b) by 1081 days.

(21) Appl. No.: 11/690,981

(22) Filed: Mar. 26, 2007

(65) Prior Publication Data

US 2007/0275924 A1    Nov. 29, 2007

Related U.S. Application Data

(60) Provisional application No. 60/785,800, filed on Mar. 24, 2006.

(51) Int. Cl.
| | | |
|---|---|---|
| A61K 45/00 | (2006.01) |
| A61K 47/44 | (2006.01) |
| C07K 1/00 | (2006.01) |
| C07K 14/00 | (2006.01) |
| C07K 17/00 | (2006.01) |
| G01N 33/53 | (2006.01) |
| G01N 33/567 | (2006.01) |
| C12N 5/00 | (2006.01) |
| C12N 15/88 | (2006.01) |
| A61K 38/17 | (2006.01) |
| G01N 33/50 | (2006.01) |

(52) U.S. Cl.
CPC ........ G01N 33/5008 (2013.01); C12N 2810/00 (2013.01); C12N 15/88 (2013.01); A61K 38/177 (2013.01); C07K 2319/07 (2013.01)
USPC ......... 424/283.1; 530/350; 435/7.2; 435/375; 435/458

(58) Field of Classification Search
CPC ......... A61K 45/00; A61K 47/44; C07K 1/00; C07K 14/00; C07K 17/00; G01N 33/53; G01N 33/567; C12N 5/00; C12N 15/88
See application file for complete search history.

(56) References Cited

U.S. PATENT DOCUMENTS

| 5,776,770 A * | 7/1998 | Schnitzer ................... 435/317.1 |
|---|---|---|
| 6,071,533 A | 6/2000 | Papahadjopoulos et al. |
| 6,156,337 A | 12/2000 | Barenholz et al. |
| 6,303,378 B1 | 10/2001 | Bridenbaugh et al. |
| 6,749,863 B1 | 6/2004 | Chang et al. |
| 2002/0065224 A1 | 5/2002 | Bender et al. |

FOREIGN PATENT DOCUMENTS

| WO | 9709055 | 3/1997 |
|---|---|---|
| WO | 0221140 | 3/2002 |

OTHER PUBLICATIONS

Fielding et al., Lipid Res. Aug. 1997;38(8):1503-21.*
Tagawa et al., (J Cell Biol. Aug. 29, 2005;170(5):769-79).*
Definition of "liposome" Steadman's Medical Dictionary 27th Ed (Lippincott Williams & Wilkins. 2000).*
Ashok et al., (J Virol. Jan. 2003; 77(2): 1347-1356).*
Carillo and Lipman, "The multiple sequence alignment problem in biology", SIAM J. Applied Math., 48(5):1073-82 (1988).
Clark and Shay, "Mitochondrial transformation of mammalian cells", Nature, 295(5850):605-7 (1982).
Cline and Henry, "Import and routing of nucleus-encoded chloroplast proteins", Annual Review of Cell & Developmental Biology, 12:1-26 (1996).
Cohen, et al., "Caveolin-1 expression is essential for proper nonshivering thermogenesis in brown adipose tissue", Diabetes, 54(3):679-86 (2005).
Emanuelson, et al., "Predicting subcellular localization of proteins based on their N-terminal amino acid sequence", Journal of Molecular Biology, 300(4):1005-16 (2000).
Garofalo, et al., "Lipid microdomains contribute to apoptosis-associated modifications of mitochondria in T cells", Cell Death Differ., 12(11):1378-89 (2005).
Lee, et al., "Identification of a signal that distinguishes between the chloroplast outer envelope membrane and the endomembrane system in vivo", Plant Cell, 13(10):2175-90 (2001).
Li, et al., "Na+-H+ exchanger 3 (NHE3) is present in lipid rafts in the rabbit ileal brush border: a role for rafts in trafficking and rapid stimulation of NHE3", J. Physiol., 537(Pt. 2):537-52 (2001).
Mordenti and Chappell, "The use of interspecies scaling in toxicokinetics" In Toxicokinetics and New Drug Development, Yacobi et al., Eds., Pergamon Press, New York, pp. 42-96 (1989).
Needelman and Wunsch, "A general method applicable to the search for similarities in the amino acid sequence of two proteins", J. Mol. Biol., 48(3): 443-453 (1970).
Prokisch, et al., "MitoP2, the mitochondrial proteome database—now including mouse data", Nucleic Acids Res., 34(Database issue) D705-11 (2006).
Simons and Ikonen, "Functional rafts in cell membranes", Nature, 387(6633):569-572 (1997).
Smart, et al., "Caveolins, liquid-ordered domains, and signal transduction", Mol. Cell Biol., 19(11):7289-304 (1999).
Stojanovski, et al., "Levels of human Fis1 at the mitochondrial outer membrane regulate mitochondrial morphology", J. Cell Sci., 117(Pt 7):1201-10 (2004).
Carver, et al., "Caveolae: Mining little caves for new cancer targets", Nature Reviews Cancer, 3(8):571-81 (2003).
Husain, et al., "Real-time confocal imaging of caveolae trafficking in endothelial cells", FASEB J., 20(5):A843-A844 (2006).
Li, et al., "Probing caveolar function with GFP-caveolin", J. Am Soc Nephrology, Abstract issue 11:32A (2000).
Ren, et al., "Association of caveolin-1 with lipid rafts depends on several domains", FASEB J., 17:4-5 (2003).

* cited by examiner

Primary Examiner — Cherie M Stanfield
(74) Attorney, Agent, or Firm — Pabst Patent Group LLP

(57) ABSTRACT

Compositions and methods for delivering cargo to cells are provided. One aspect provides a synthetic vesicle containing caveolin 1 or a fragment thereof in an amount effective to form lipid rafts in the vesicle. The synthetic vesicles can be used to deliver polynucleotides, proteins, therapeutic agents, or a combination thereof to specific membrane-bound compartments of a cell. In certain aspects, the synthetic vesicles can deliver cargo to cellular organelles such as mitochondria.

9 Claims, No Drawings

SEQUENCE LISTING

```
<160> NUMBER OF SEQ ID NOS: 14

<210> SEQ ID NO 1
<211> LENGTH: 178
<212> TYPE: PRT
<213> ORGANISM: Homo sapiens

<400> SEQUENCE: 1

Met Ser Gly Gly Lys Tyr Val Asp Ser Glu Gly His Leu Tyr Thr Val
1               5                   10                  15
```

-continued

```
Pro Ile Arg Glu Gln Gly Asn Ile Tyr Lys Pro Asn Asn Lys Ala Met
            20                  25                  30

Ala Asp Glu Leu Ser Glu Lys Gln Val Tyr Asp Ala His Thr Lys Glu
        35                  40                  45

Ile Asp Leu Val Asn Arg Asp Pro Lys His Leu Asn Asp Asp Val Val
    50                  55                  60

Lys Ile Asp Phe Glu Asp Val Ile Ala Glu Pro Gly Thr His Ser
65                  70                  75                  80

Phe His Gly Ile Trp Lys Ala Ser Phe Thr Thr Phe Thr Val Thr Lys
                85                  90                  95

Tyr Trp Phe Tyr Arg Leu Leu Ser Ala Leu Phe Gly Ile Pro Met Ala
            100                 105                 110

Leu Ile Trp Gly Ile Tyr Phe Ala Ile Leu Ser Phe Leu His Ile Trp
        115                 120                 125

Ala Val Val Pro Cys Ile Lys Ser Phe Leu Ile Glu Ile Gln Cys Thr
    130                 135                 140

Ser Arg Val Tyr Ser Ile Tyr Val His Thr Val Cys Asp Pro Leu Phe
145                 150                 155                 160

Glu Ala Val Gly Lys Ile Phe Ser Asn Val Arg Ile Asn Leu Gln Lys
                165                 170                 175

Glu Ile

<210> SEQ ID NO 2
<211> LENGTH: 11
<212> TYPE: PRT
<213> ORGANISM: Human immunodeficiency virus

<400> SEQUENCE: 2

Tyr Gly Arg Lys Lys Arg Arg Gln Arg Arg Arg
1               5                   10

<210> SEQ ID NO 3
<211> LENGTH: 9
<212> TYPE: PRT
<213> ORGANISM: human immunodeficiency virus

<400> SEQUENCE: 3

Arg Lys Lys Arg Arg Gln Arg Arg Arg
1               5

<210> SEQ ID NO 4
<211> LENGTH: 12
<212> TYPE: PRT
<213> ORGANISM: artificial sequence
<220> FEATURE:
<223> OTHER INFORMATION: Synthetic protein transduction domain

<400> SEQUENCE: 4

Arg Arg Gln Arg Arg Thr Ser Lys Leu Met Lys Arg
1               5                   10

<210> SEQ ID NO 5
<211> LENGTH: 16
<212> TYPE: PRT
<213> ORGANISM: artificial sequence
<220> FEATURE:
<223> OTHER INFORMATION: synthetic protein transduction domain

<400> SEQUENCE: 5

Ala Ala Val Ala Leu Leu Pro Ala Val Leu Leu Ala Leu Leu Ala Ala
1               5                   10                  15
```

<210> SEQ ID NO 6
<211> LENGTH: 16
<212> TYPE: PRT
<213> ORGANISM: artificial sequence
<220> FEATURE:
<223> OTHER INFORMATION: synthetic protein transduction domain

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 16
<212> TYPE: PRT
<213> ORGANISM: artificial sequence
<220> FEATURE:
<223> OTHER INFORMATION: synthetic protein transduction domain

<400> SEQUENCE: 7

Arg Val Ile Arg Val Trp Phe Gln Asn Lys Arg Cys Lys Asp Lys Lys
1               5                   10                  15

<210> SEQ ID NO 8
<211> LENGTH: 21
<212> TYPE: RNA
<213> ORGANISM: artificial sequence
<220> FEATURE:
<223> OTHER INFORMATION: synthetic siRNA

<400> SEQUENCE: 8
agacgagcug agcgagaagc a                                          21

<210> SEQ ID NO 9
<211> LENGTH: 21
<212> TYPE: RNA
<213> ORGANISM: artificial sequence
<220> FEATURE:
<223> OTHER INFORMATION: synthetic siRNA

<400> SEQUENCE: 9
cuucucgcuc agcucgucug c                                          21

<210> SEQ ID NO 10
<211> LENGTH: 21
<212> TYPE: DNA
<213> ORGANISM: artificial sequence
<220> FEATURE:
<223> OTHER INFORMATION: synthetic siRNA

<400> SEQUENCE: 10
ttacggatgt catcattgta c                                          21

<210> SEQ ID NO 11
<211> LENGTH: 21
<212> TYPE: DNA
<213> ORGANISM: artificial sequence
<220> FEATURE:
<223> OTHER INFORMATION: synthetic siRNA

<400> SEQUENCE: 11
aaggggatta ctgcaatctt t                                          21

<210> SEQ ID NO 12
<211> LENGTH: 21
<212> TYPE: DNA

```
<213> ORGANISM: artificial sequence
<220> FEATURE:
<223> OTHER INFORMATION: synthetic siRNA

<400> SEQUENCE: 12
aaagattgca gtaatccct t                                              21

<210> SEQ ID NO 13
<211> LENGTH: 21
<212> TYPE: DNA
<213> ORGANISM: artificial sequence
<220> FEATURE:
<223> OTHER INFORMATION: synthetic siRNA

<400> SEQUENCE: 13
gtataatgat gatatttgta a                                             21

<210> SEQ ID NO 14
<211> LENGTH: 11
<212> TYPE: PRT
<213> ORGANISM: Artificial Sequence
<220> FEATURE:
<223> OTHER INFORMATION: synthetic protein transduction domain

<400> SEQUENCE: 14

Tyr Ala Arg Ala Ala Ala Arg Gln Ala Arg Ala
1               5                   10
```

SYNTHETIC LIPID RAFTS AND METHODS OF USE

CROSS-REFERENCE TO RELATED APPLICATION

This application claims priority to and benefit of U.S. Provisional patent application No. 60/785,800 filed on Mar. 24, 2006, and where permissible is incorporated by reference herein in its entirety.

REFERENCE TO SEQUENCE LISTING

The Sequence Listing submitted May 25, 2011 as a text file named "GNC_0005_Updated_Sequence_Listing.txt," created on Mar. 25, 2011, and having a size of 4,586 bytes is hereby incorporated by reference pursuant to 37 C.F.R. §1.52 (e)(5).

FIELD OF THE INVENTION

Aspects of the invention are generally directed to methods and compositions for delivering cargo to a cell, in particular, to synthetic vesicles containing lipid rafts for delivering small molecules, polypeptides, or polynucleotides to the interior of a cell.

BACKGROUND OF THE INVENTION

The facilitated transfer of nucleic acids into cells is one of the most valuable and frequently used techniques of modern biological science. In today's laboratories, this technique is performed for multiple purposes, including gene therapy research, studies of gene regulation, protein structure/function analyses, as well as production of recombinant proteins. There are currently a wide variety of gene transfer methods available but each has specific shortcomings.

Nucleic acids can be delivered to cells using chemical means such as DEAE-dextran-Diethylaminoethyl-dextran (DEAE-Dextran), calcium phosphate precipitation, cationic lipids (lipofection), polyethylenimine (PEI), and with targeting proteins and peptides in combination with cationic lipids. Unfortunately, there are a limited range of cell types in which DEAE-dextran works effectively. The calcium phosphate method is sensitive to slight changes in buffer salt concentrations, temperature, and pH, and has relatively poor transfection efficiency compared to newer transfection methods, especially in suspension cells such as lymphocytes. With regard to cationic lipids, several types of primary cultured cells, such as primary neurons, primary dendritic cells, and primary endothelial cells remain recalcitrant to non-viral mediated transfection methods, including cationic lipids. Moreover, the application of cationic lipid to in vivo gene delivery remains difficult.

Existing targeting proteins are typically used in combination with cationic lipids. For example protamine sulfate with DNA followed by addition of cationic lipids has been reported to enhance transgene expression in cultured cells compared to DNA delivery with lipids alone. Unfortunately, certain viral targeting proteins can cause immunogenic responses in hosts. Additionally, the interaction of cationic lipids with serum proteins can significantly reduce the efficiency of transfection.

It is an object of the invention to provide synthetic compositions containing lipid rafts and methods of use thereof for delivering cargo to cells.

It is still another object of the invention to provide methods for treating a disease, disorder, or a symptom of a disease or disorder using synthetic compositions containing lipid rafts.

It is yet another object of the invention to provide synthetic compositions containing lipid rafts for transfecting cells in vitro or in vivo.

It is another object to provide methods and compositions for identifying modulators of vesicular traffic.

SUMMARY OF THE INVENTION

Synthetic vehicles containing lipid rafts are provided. The vehicles or vesicles are suitable for delivering cargo to cells, intracellular membranes, or membrane bound structures such as organelles. A representative vehicle includes one or more lipids in combination with one or more polypeptides or fragments thereof having at least about 80% sequence identity with SEQ ID NO:1 (caveolin 1) that form a vesicle. Caveolin 1 is typically present in the vesicle in an amount effective to form lipid rafts in the vesicle and facilitate delivery of cargo to an intracellular region of a cell, for example from about 5 nM to about 100 μM. The cargo can be a drug or small molecule therapeutic, polynucleotide, polypeptide or a combination thereof.

Another aspect provides a method for transfecting a cell with a target polynucleotide by contacting the cell with the disclosed vehicles, wherein the vehicle comprises a polynucleotide. The polynucleotide is expressed in the cell or organelle of the cell.

Still another aspect provides a method for transfecting a cell with a target polynucleotide including the step of contacting the cell with a recombinant mitochondrion under conditions that promote mitochondrial fusion, wherein the recombinant mitochondrion comprises the target polynucleotide. The mitochondria can be from the same or different organism.

One aspect provides a fusion protein comprising an amino acid sequence according to SEQ ID NO:1 or a fragment thereof operably linked to a reporter and a targeting polypeptide. The fusion protein can be used to follow membrane trafficking in a cell. The fusion protein can be used to manipulate or redirect membrane trafficking in a cell.

Yet another aspect provides a method for screening for inhibitors of vesicular traffic by contacting a cell expressing a disclosed fusion protein with a test compound and determining the location of the fusion protein by detecting a signal from a reporter moiety of the fusion protein. The location of the fusion protein in cells contacted with the test compound can be compared to the location of the fusion protein in control cells. Decreased distribution of the fusion protein relative to control cells indicates the test compound is an inhibitor of vesicular traffic; whereas, increased distribution of the fusion protein relative to control cells indicates the test compound is an agonist of vesicular traffic.

Another aspect provides a method for treating a pathology comprising administering the disclosed vehicles to a host in need thereof, wherein the vehicle comprises a polynucleotide, therapeutic agent, polypeptide, or combination thereof.

DETAILED DESCRIPTION

Definitions

Unless otherwise noted, technical terms are used according to conventional usage. Definitions of common terms in molecular biology may be found in Lewin, Genes VII, published by Oxford University Press, 2000; Kendrew et al.

(eds.), The Encyclopedia of Molecular Biology, published by Wiley-Interscience, 1999; and Robert A. Meyers (ed.), Molecular Biology and Biotechnology, a Comprehensive Desk Reference, published by VCH Publishers, Inc., 1995; Ausubel et al. (1987) Current Protocols in Molecular Biology, Green Publishing; Sambrook and Russell, (2001) Molecular Cloning: A Laboratory Manual 3rd edition.

In order to facilitate understanding of the disclosure, the following definitions are provided:

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Representative small molecules include, but are not limited to protease inhibitors, antibiotics, anti-oxidants, vitamins, co-factors, chemotherapeutic agents, cytotoxins, hormones, transcription factors, anti-inflammatory agents, or combinations thereof.

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamnine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chains substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also means the degree of sequence relatedness between polypeptide as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison, Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

As used herein, the term "low stringency" refers to conditions that permit a polynucleotide or polypeptide to bind to another substance with little or no sequence specificity.

As used herein, the term "purified" and like terms relate to the isolation of a molecule or compound in a form that is substantially free (at least 60% free, preferably 75% free, and most preferably 90% free) from other components normally associated with the molecule or compound in a native environment. As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the term "treating" includes alleviating the symptoms associated with a specific disorder or condition and/or preventing or eliminating said symptoms.

"Operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will direct the linked protein to be localized at the specific organelle.

"Localization Signal or Sequence or Domain" or "Targeting Signal or Sequence or Domain" are used interchangeably and refer to a signal that directs a molecule to a specific cell, tissue, organelle, or intracellular region. The signal can be polynucleotide, polypeptide, or carbohydrate moiety or can be an organic or inorganic compound sufficient to direct an attached molecule to a desired location. Exemplary organelle localization signals include nuclear localization signals known in the art and other organelle localization signals known in the art such as those provided in Tables 2 and 3 and described in Emanuelson et al., Predicting Subcellular Localization of Proteins Based on Their N-terminal Amino Acid Sequence, *Journal of Molecular Biology*, 300(4):1005-16, 2000 July 21, and in Cline and Henry, Import and Routing of Nucleus-encoded Chloroplast Proteins, *Annual Review of Cell & Developmental Biology*, 12:1-26, 1996, the disclosures of which are incorporated herein by reference in their entirety. It will be appreciated that the entire sequence listed in Tables 2 and 3 need not be included, and modifications including truncations of these sequences are within the scope of the disclosure provided the sequences operate to direct a linked molecule to a specific organelle. Organelle localization signals of the present disclosure can have 80 to 100% identity to the sequences in Tables 2 and 3. One class of suitable organelle localization signals include those that do not interact with the targeted organelle in a receptor:ligand mechanism. For example, organelle localization signals include signals having or conferring a net charge, for example a positive charge. Positively charged signals can be used to target negatively charged organelles such as the mitochondria. Negatively charged signals can be used to target positively charged organelles.

"Protein Transduction Domain" or PTD refers to a polypeptide, polynucleotide, carbohydrate, or organic or inorganic compounds that facilitates traversing a lipid bilayer, micelle, cell membrane, organelle membrane, or vesicle membrane. A PTD attached to another molecule facilitates the molecule traversing membranes, for example going from extracellular space to intracellular space, or cytosol to within an organelle. Exemplary PTDs include but are not limited to HIV TATYGRKKRRQRRR (SEQ ID NO:2) or RKKRRQRRR (SEQ ID NO:3); 7-11 Arginine residues, or positively charged polypeptides or polynucleotides having 8-15 residues, preferably 9-11 residues; YARAAARQARA (SEQ ID NO:14); RRQRRTSKLMKR (SEQ ID NO:4); AAVALLPAVLLALLAA (SEQ ID NO:5); RQIKIWFQNR-RMKWKK (SEQ ID NO:6) or RVIRVWFQNKRCKDKK (SEQ ID NO:7).

As used herein, the term "exogenous DNA" or "exogenous nucleic acid sequence" or "exogenous polynucleotide" refers to a nucleic acid sequence that was introduced into a cell or organelle from an external source. Typically the introduced exogenous sequence is a recombinant sequence.

As used herein, the term "transfection" refers to the introduction of a nucleic acid sequence into the interior of a membrane enclosed space of a living cell, including introduction of the nucleic acid sequence into the cytosol of a cell as well as the interior space of a mitochondria, nucleus or chloroplast. The nucleic acid may be in the form of naked DNA or RNA, associated with various proteins or the nucleic acid may be incorporated into a vector.

As used herein, the term "vector" is used in reference to a vehicle used to introduce a nucleic acid sequence into a cell. A viral vector is virus that has been modified to allow recombinant DNA sequences to be introduced into host cells or cell organelles.

As used herein, the term "organelle" refers to cellular membrane bound structures such as the chloroplast, mitochondrion, and nucleus. The term "organelle" includes natural and synthetic organelles.

As used herein, the term "non-nuclear organelle" refers to any cellular membrane bound structure present in a cell, except the nucleus.

As used herein, the term "polynucleotide" generally refers to any polyribonucleotide or polydeoxribonucleotide, which may be unmodified RNA or DNA or modified RNA or DNA. Thus, for instance, polynucleotides as used herein refers to, among others, single- and double-stranded DNA. DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The term "nucleic acid" or "nucleic acid sequence" also encompasses a polynucleotide as defined above.

In addition, polynucleotide as used herein refers to triple-stranded regions comprising RNA and DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified based. Thus, DNAs or RNAs with backbones modified for stability or for other reasons are "polynucleotides" as that term is intended herein. Moreover, DNAs or RNAs comprising unusual bases, such as inosine, or modified based, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

"Oligonucleotide(s)" refers to relatively short polynucleotides. Often the term refers to single-stranded deoxyribonucleotides, but it can refer as well to single- or double-stranded ribonucleotides, RNA:DNA hybrids and double-stranded DNAs, among others.

I. Synthetic Vesicle Compositions

It has been discovered that lipid rafts comprising caveolin-1 contribute to intracellular transport between vesicles, organelles, and other membranes and membrane bound regions. Moreover, it has been discovered that synthetic cargo delivery vehicles comprising caveolin 1 or a fragment thereof in combination with one or more lipids, for example cationic lipids, are useful for delivering cargo from extracellular space to intracellular space, between cellular membranes as well as to or between specific organelles such as the mitochondrion nucleus, or other organelle. One embodiment provides synthetic vehicles containing lipid rafts. The synthetic vehicles can be synthetic vesicles or liposomes containing lipid rafts. The lipid rafts can be formed by one or more proteins inserted into the vehicle interacting with lipids forming the vehicle. A representative protein is caveolin 1, a lipid raft forming fragment thereof, or variant thereof. If the vesicle is bilayered, the lipid rafts can be on the outer layer, inner layer, or both.

A. Lipid Rafts

In one embodiment, the synthetic vesicles include one or more lipid rafts. In one embodiment, artificial lipid raft compositions include cholesterol, and one or more lipids selected from the group consisting of sphingomyelin, gangliosides, phosphatidylethanolamine, phosphatidylserine, phosphatidylcholine, phosphatidylinositol, and ceramides. Representative lipid compositions are provided in Table 1 (Smart E J, et al. Caveolins, liquid-ordered domains, and signal transduction. Mol Cell Biol. 19(11):7289-304 (1999)).

TABLE 1

Exemplary Lipid Content of Artificial Lipid Raft Compositions

| Lipid | % of lipid in vesicle |
|---|---|
| Cholesterol | 10-26 or 7 |
| Sphingomyelin | 96 or 50-70 |
| Gangliosides | 30-67 |
| Phosphatidylethanolamine | 6-15 |
| Phosphatidylserine | 10-30 |
| Phosphatidylcholine | 5-25 |
| Phosphatidylinositol | 5-25 |
| Phosphatidylinositol P2 | 15-50 |
| Ceramide | 15-50 |
| Diacyl-glycerol | 15-50 |

Note that the percentage of component is relative to the whole-cell lipid content.

Lipid rafts are localized regions of elevated cholesterol and glycosphingolipid content within cell membranes, most notably the plasma membrane, though Golgi, endoplasmic reticulum, and the nucleus also possess lipid rafts (Li et al., J Physiol. 537(Pt 2):537-52 (2001)). The acyl groups of the phospholipids present in lipid rafts and caveolae are more highly saturated than those in the surrounding membrane. This allows close packing of these phospholipid side chains with the saturated acyl chains of sphingolipids and enhances phase (liquid-solid) separation. Due to the presence of cholesterol, a liquid ordered domain is formed that exhibits less fluidity than the surrounding plasma membrane, hence the term lipid raft in a sea of more liquid phospholipids. Caveolae, small plasma membrane invaginations that are coated with the cholesterol-associated protein caveolin, are a subset of lipid rafts. The presence within lipid rafts and caveolae of a variety of membrane proteins involved in cell signaling, including many receptors, has led to the consensus that these lipid domains play an important role in the process of signal transduction by colocalizing interacting proteins into contiguous microdomains. These microdomains have been termed signalosomes, as they provide the nano-architectural framework for the transduction of extracellular signals.

Proteins that have shown association to the lipid rafts include glycosylphosphatidylinositol (GPI)-anchored proteins, doubly-acylated tyrosine kinases of the Src family, and transmembrane proteins. This association can at least be partially contributed to the acylated, saturated tails of both the tyrosine kinases and the GPI-anchored proteins, which matches the properties of sphingolipids more so than the rest of the membrane (Simons, K., Ikonen, E. Nature 387(6633): 569-572 (1997)). While these proteins tend to continuously be present in lipid rafts, there are others that associate with lipid rafts only when the protein is activated. Some examples of these include, but are not limited to, B cell receptors (BCRs), T cell receptors (TCRs), PAG, and an enzyme called CD39. Other proteins that associate with or help form lipid rafts include but are not limited to MARKS, CAP, GAP-43, or combinations thereof. Proteins are typically present in an amount varying from about 5 nM to about 100 μM.

In one embodiment the lipid rafts of a synthetic vesicle include one more of cholesterol, glycoshingolipid, arachidonic acid, plasmenylethanolamine, caveolin 1 and 2, heterotrimeric G-proteins and monomeric G-proteins, EGF & PDGF receptors, Fyn, GPI-linked enzymes, integrins, Flotillin, or combinations thereof.

In one embodiment the lipid rafts of a synthetic vesicle include one more of cholesterol, glycoshingolipid, and other anionic phospholipids. In this embodiment the lipids forming the lipid rafts include less than about 10% phosphatidylinositol, typically less than about 5% phosphatidylinositol.

B. Caveolae

Another embodiment provides synthetic caveolae capable of delivering cargo to an intercellular organelle or vesicle. Caveolae are vesicular organelles (50-100-nm in diameter) which form invaginated, active micro-domains in the plasma membrane and are believed to be involved in receptor-mediated uptake of molecules, a process called potocytosis. Caveolins are the structural proteins that are both necessary and sufficient for the formation of caveolae membrane domains. Caveolins 1 and 2 are co-expressed in most cell types, while the expression of caveolin-3 is muscle-specific. Within the microdomain of caveolae, caveolins interact with a variety of downstream signaling molecules, including Src-family tyrosine kinases, p42/44 mitogen activated protein (MAP) kinase, and endothelial nitric oxide synthase (eNOS), and hold these signal transducers in the inactive conformation until activation by an appropriate stimulus. Caveolins are also involved in the subcellular targeting of caveolae, enabling specific signalosomes to be targeted to the Golgi, ER, or nucleus. Mitochondria have been shown to possess a significant amount of Caveolin 1, though it is unknown what role it may be serving within mitochondria. In fact, Caveolin 1 knockout mice tissue possesses dramatic perturbations in mitochondria, which were enlarged, had little matrix material and few cristae despite possessing normal oxidative metabolism (Cohen et al., 2005).

One embodiment provides a vehicle for delivering cargo to a cell, intracellular vesicle, organelle, or intracellular membrane. The vehicle includes one or more lipids and caveolin-1 (Cav1), a fragment of Cav1, or a variant of Cav1 effective to produce lipid rafts in the vehicle, for example from about 5 nM to about 100 µM. The caveolin can be isolated from a natural or source or can be recombinant caveolin. Alternatively, the caveolin peptides or proteins can be synthesized using standard peptide synthesis techniques. The vehicle optionally includes additional proteins for example Cav2 and/or Cav3 in amounts effective to produce lipid rafts in the vehicle. In certain embodiments, the lipids form a spherical structure having an interior region. For example, the vehicle can form unilamellar, bilamellar, or multilaminer vesicles. Unilamellar vesicles include micelles, and bilamellar vesicles include liposomes. The interior region can harbor cargo to be delivered to a cell, or to an organelle within the cell. Cargo includes polypeptides, polynucleotides, or other compounds that cannot passively or easily traverse a cell membrane.

Suitable lipids include, but are not limited to cationic lipids optionally in combination with a stabilizing lipid or agent. Exemplary lipids include phosphatidylcholine, phosphatidylserine, phosphatidylethanolamine, phosphatidyl glycerol, sphingomyelin, cholesterol, ioleoylphosphatidylethanolamine, dioleoydimethylammonium chloride (DODAC), cholesteryl hemisuccinate, 3-[N—(N',N'-dimethylaminoethane)-carbamoyl]cholesterol hydrochloride (DC-Chol), dioleoylphosphatidic acid (DOPA), 1,2-Dioleoyl-sn-Glycero-3-Phosphoethanolamine (DOPE), Dimethyldioctadecylammonium Bromide (DDAB), 1,2-Dioleoyl-3-Trimethylammonium-Propane (DOTAP), 1,2-Dioleoyl-3-Dimethylammonium-Propane (DODAP), 3β-[N—(N',N'-Dimethylaminoethane)-carbamoyl]Cholesterol (DC-Cholesterol), 1,2-Dioleoyl-sn-Glycero-3-Phosphoethanolamine-N-(glutaryl) (DOPE-Glutaric acid) or a combination thereof. Stabilizing lipids include cholesterol and modified forms of cholesterol.

Another embodiment provides a vehicle comprising one or more lipids in combination with one or more polypeptides or fragments thereof having at least about 80%, 85%, 90%, 95%, 99% or more sequence identity with SEQ ID NO:1 (caveolin 1), wherein the one or more polypeptides or fragments thereof are present in an amount effective to facilitate delivery of cargo to an intracellular region of a cell.

Modifications and changes can be made in the amino acid sequence according to SEQ ID NO:1 and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamnine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Trp: Tyr), (Tyr: Trp, Phe), and (Val: Ile, Leu). Embodiments of this disclosure thus contemplate functional or biological equivalents of caveolin1 ass set forth above. In particular, embodiments of the polypeptides can include variants having about 50%, 60%, 70%, 80%, 90%, 95%, and 99% or more sequence identity to the polypeptide according to SEQ ID NO:1.

The disclosed vehicles can further comprise a targeting signal. Targeting signals include peptide signals such as nuclear localization signals, mitochondrial localization signals, chloroplast localization signals, or a combination thereof. Alternatively, the targeting signal can be a chemical group that confers a charge to the vehicle, for example a positive charge. The targeting signal can be incorporated into the caveolin-1 polypeptide. In one embodiment, the targeting signal is a antibody or antigen binding antibody fragment. Suitable targeting signals are provided in Table 2. The sequences of these targeting signals are known in the art and available for example from Genbank or other publicly available databases.

C. Cargo

The cargo to be delivered to a cell or organelle typically comprises a polynucleotide, polypeptide, small organic molecule, or a combination thereof. The polynucleotide can encode a functional protein, for example a mitochondrial respiratory chain component, a therapeutic protein, siRNA, anti-sense DNA, or a combination thereof. Polypeptide cargo can include enzymes, antibodies, antigen-binding antibody fragments, transcription factors, growth factors, peptide hormones, and combinations thereof. Polynucleotide cargo can comprise DNA, RNA, or a combination thereof. In some embodiments, the polynucleotide cargo comprises anti-sense DNA, siRNA, microRNA, or a combination thereof. Polynucleotide cargo includes vectors such as expression vectors and DNA constructs that can be transcribed to produce mRNA that is translated by cellular translation machinery. The vectors can include inducible promoters, tissue specific promoters, and other regulatory elements known in the art needed to control expression of a protein or nucleic acid encoded by the vector.

Loading of cargo into the synthetic vehicle or synthetic vesicle includes methods described in U.S. Pat. No. 6,156, 337. A representative method includes, but is not limited to a) mixing amphiphatic substances, such as lipids suitable for forming vesicles in water-immiscible organic solvents;

b) removing of the solvent in presence of a solid support, alternatively, dried amphiphatic substances or mixtures thereof can be used in any form (powder, granular, etc.) directly, c) taking up the product of step b) into a solution of the biopolymeric substances in a physiologically compatible solution d) adding an organic solvent having solubilizing or dispersing properties, as well as e) drying the fraction obtained in step d) under conditions retaining the function of the biopolymeric substances.

The cargo can be directed to a specific intracellular region or organelle such as the mitochondrion, nucleus, golgi, endoplasmic reticulum, lysosome, or peroxisome.

Suitable cargo also includes pharmaceutically active agents. Suitable classes of active agents include, but are not limited to, antibiotic agents, antimicrobial agents, anti-acne agents, antibacterial agents, antifungal agents, growth factors, cytokines, chemokines, morphogens, antiviral agents, steroidal anti-inflammatory agents, non-steroidal anti-inflammatory agents, anesthetic agents, antipruriginous agents, antiprotozoal agents, anti-oxidants, antihistamines, vitamins, and hormones.

The compositions optionally contain one or more additional pharmaceutically active agents. Suitable classes of active agents include, but are not limited to, antibiotic agents, antimicrobial agents, anti-acne agents, antibacterial agents, antifungal agents, antiviral agents, steroidal anti-inflammatory agents, non-steroidal anti-inflammatory agents, anesthetic agents, antipruriginous agents, antiprotozoal agents, anti-oxidants, antihistamines, vitamins, and hormones.

i. Antibiotics

Representative antibiotics include, without limitation, benzoyl peroxide, octopirox, erythromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; and bile salts such as scymnol sulfate and its derivatives, deoxycholate and cholate. The antibiotic can be an antifungal agent. Suitable antifungal agents include, but are not limited to, clotrimazole, econazole, ketoconazole, itraconazole, miconazole, oxiconazole, sulconazole, butenafine, naftifine, terbinafine, undecylinic acid, tolnaftate, and nystatin.

The concentration of the antibiotic is from about 0.01% to about 20%, preferably from about 1% to about 15%, more preferably from about 6% to about 12% by weight of the final composition.

ii. Non-Steroidal Anti-Inflammatory Agents

Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamate, a flufenamic acid derivative, is particularly useful for topical application.

iii. Steroidal Anti-Inflammatory Agents

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

iv. Antimicrobial Agents

Suitable antimicrobial agents include, but are not limited to, antibacterial, antifungal, antiprotozoal and antiviral agents, such as beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, famesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paramomycin sulfate, streptomycin sulfate, tobramycin sulfate, miconazole hydrochloride, amanfadine hydrochloride, amanfadine sulfate, triclosan, octopirox, nystatin, tolnaftate, clotrimazole, anidulafungin, micafungin, voriconazole, lanoconazole, ciclopirox and mixtures thereof.

II. Methods of Manufacture

The vehicles containing lipid rafts can be produced using conventional methods for producing liposomes or lipid vesicles. For example, lipid components are dissolved in a suitable solvent such as chloroform to a convenient working concentration (1-10 mg/mL). Representative lipids include, but are not limited to phosphatidylcholine, phosphatidylserine, phosphatidylethanolamine, phosphatidyl glycerol, sphingomyelin, cholesterol, ioleoylphosphatidylethanolamine, dioleoydimethylammonium chloride (DODAC), cholesteryl hemisuccinate, 3-[N—(N',N'-dimethylaminoethane)-carbamoyl]cholesterol hydrochloride (DC-Chol), dioleoylphosphatidic acid (DOPA), 1,2-Dioleoyl-sn-Glycero-3-Phosphoethanolamine (DOPE), Dimethyldioctadecylammonium Bromide (DDAB), 1,2-Dioleoyl-3-Trimethylammonium-Propane (DOTAP), 1,2-Dioleoyl-3-Dimethylammonium-Propane (DODAP), 3β-[N—(N',N'-Dimethylaminoethane)-carbamoyl]Cholesterol (DC-Cholesterol), 1,2-Dioleoyl-sn-Glycero-3-Phosphoethanolamine-N-(glutaryl) (DOPE-Glutaric acid) or a combination thereof.

An aliquot of each component can be placed in a glass vial using for example, a glass syringe. The components are mixed in the glass vial, and the solvent is removed for example by vacuum suction. The lipids are resuspended in distilled water at twice the final lipid concentration. Caveolin 1, or a variant thereof, is the added to the aqueous suspension to a desired concentration. The suspension can be sonicated to clarity with an equal volume of a desired buffer (e.g., 308 mM NaCl, 40 mM Hepes, pH 7.4). The solution can be further sonicated if necessary and sterilized using conventional methods.

Cargo can be added to the delivery vehicles during or after preparation of the vehicles using conventional techniques. For example, the cargo can be present during the formation of the vesicles or after the formation of the vesicles.

The synthetic vesicles can be "small, unilamellar vesicles" or "Sonicated, Unilamellar Vesicles" which are usually prepared by sonication using a cuphorn, bath, or probe tip sonicator. The synthetic vesicles can also be "Large, Unilamellar Vesicles" and that can be prepared by a variety of methods including extrusion (LUVET or "Large, Unilamellar Vesicles prepared by Extrusion Technique"), detergent dialysis (DOV or Dialyzed Octylglucoside Vesicles), fusion of SUV (FUV or "Fused, Unilamellar Vesicles"), reverse evaporation (REV or "Reverse Evaporation Vesicles"), and ethanol injection. Unilamellar vesicles are prepared from MLV or LMV (Large, Multilamellar Vesicles), the large "onion-like" structures formed when amphiphilic lipids are hydrated. SUV are typically 15-30 nm in diameter while LUV range from 100-200 nm or larger. LUV are stable on storage, however, SUV will spontaneously fuse when they drop below the phase transition temperature of the lipid forming the vesicle.

III. Methods of Use

The disclosed cargo delivery vehicles can be used to deliver small molecules, in particular therapeutic compounds to the interior of a cell. In certain embodiments, the delivery vehicles deliver a drug or compound to an organelle, for example a mitochondrion, chloroplast, or nucleus. Typically the small molecule to be delivered is not able to readily cross the extracellular membrane because of charge, size, or a combination thereof. The cargo can be suspended in a solvent, carrier, or solublizing agent and the resulting combination can be loaded into the delivery vehicle. The disclosed vehicles can increase the amount of cargo delivered to a specific organelle compared to controls.

Other embodiments of the present disclosure provide compositions and methods applicable for gene therapy protocols and the treatment of gene related diseases or disorders. Organelle dysfunction can also be treated or reduced using the disclosed compositions and methods. In particular, problems with mitochondria or chloroplasts can result in disease. Mitochondrial diseases result from failures of the mitochondria, specialized compartments present in every cell of the body except red blood cells. Cell injury and even cell death are result from mitochondrial failure. If this process is repeated throughout the body, whole systems begin to fail, and the life of the person in whom this is happening is severely compromised. The disease can be in children, for example individuals less that 18 years of age, typically less than 12 years of age, or adults, for example individuals 18 years of age or more. Thus, embodiments of the present disclosure are directed to treating a host diagnosed with an organelle related disease, in particular a mitochondrial disease, by introducing a vector into the host cell wherein the vector specifically binds to the organelle and wherein the vector comprises a nucleic acid encoding mitochondrial protein or peptide. The present disclosure encompasses manipulating, augmenting or replacing portions of the mammalian cell mitochondrial genome to treat diseases caused by mitochondrial genetic defects or abnormalities.

Suitable genetic based diseases that can be treated with the compositions disclosed herein include but are not limited to:

Mitochondrial Disease:

Alpers Disease; Barth syndrome; β-oxidation defects; carnitine-acyl-carnitine deficiency; carnitine deficiency; co-enzyme Q10 deficiency; Complex I deficiency; Complex II deficiency; Complex III deficiency; Complex IV deficiency; Complex V deficiency; cytochrome c oxidase (COX) deficiency, LHON—Leber Hereditary Optic Neuropathy; MM—Mitochondrial Myopathy; LIMM—Lethal Infantile Mitochondrial Myopathy; MMC—Maternal Myopathy and Cardiomyopathy; NARP—Neurogenic muscle weakness, Ataxia, and Retinitis Pigmentosa; Leigh Disease; FICP—Fatal Infantile Cardiomyopathy Plus, a MELAS-associated cardiomyopathy; MELAS—Mitochondrial Encephalomyopathy with Lactic Acidosis and Strokelike episodes; LDYT—Leber's hereditary optic neuropathy and Dystonia; MERRF—Myoclonic Epilepsy and Ragged Red Muscle Fibers; MHCM—Maternally inherited Hypertrophic CardioMyopaty; CPEO—Chronic Progressive External Ophthalmoplegia; KSS—Kearns Sayre Syndrome; DM—Diabetes Mellitus; DMDF Diabetes Mellitus+DeaFness; CIPO—Chronic Intestinal Pseudoobstruction with myopathy and Ophthalmoplegia; DEAF—Maternally inherited DEAFness or aminoglycoside-induced DEAFness; PEM—Progressive encephalopathy; SNHL—SensoriNeural Hearing Loss; Encephalomyopathy; Mitochondrial cytopathy; Dilated Cardiomyopathy; GER—Gastrointestinal Reflux; DEMCHO—Dementia and Chorea; AMDF—Ataxia, Myoclonus; Exercise Intolerance; ESOC Epilepsy, Strokes, Optic atrophy, & Cognitive decline; FBSN Familial Bilateral Striatal Necrosis; FSGS Focal Segmental Glomerulosclerosis; LIMM Lethal Infantile Mitochondrial Myopathy; MDM Myopathy and Diabetes Mellitus; MEPR Myoclonic Epilepsy and Psychomotor Regression; MERME MERRF/MELAS overlap disease; MHCM Maternally Inherited Hypertrophic CardioMyopathy; MICM Maternally Inherited Cardiomyopathy; MILS Maternally Inherited Leigh Syndrome; Mitochondrial Encephalocardiomyopathy; Multisystem Mitochondrial Disorder (myopathy, encephalopathy, blindness, hearing loss, peripheral neuropathy); NAION Nonarteritic Anterior Ischemic Optic Neuropathy; NIDDM Non-Insulin Dependent Diabetes Mellitus; PEM Progressive Encephalopathy; PME Progressive Myoclonus Epilepsy; RTT Rett Syndrome; SIDS Sudden Infant Death Syndrome; MIDD Maternally Inherited Diabetes and Deafness; and MODY Maturity-Onset Diabetes of the Young.

Some mitochondrial diseases are a result of problems in the respiratory chain in the mitochondira. The respiratory chain consists of four large protein complexes: I, II, III and IV (cytochrome c oxidase, or COX), ATP synthase, and two small molecules that ferry around electrons, coenzyme Q10 and cytochrome c. The respiratory chain is the final step in the energy-making process in the mitochondrion where most of the ATP is generated. Mitochondrial encephalomyopathies that can be caused by deficiencies in one or more of the specific respiratory chain complexes include MELAS, MERFF, Leigh's syndrome; KSS, Pearson, PEO, NARP, MILS and MNGIE.

The mitochondrial respiratory chain is made up of proteins that come from both nuclear and mtDNA. Although only 13 of roughly 100 respiratory chain proteins come from the mtDNA, these 13 proteins contribute to every part of the respiratory chain except complex II, and 24 other mitochondrial genes are required just to manufacture those 13 proteins. Thus, a defect in either a nuclear gene or one of the 37 mitochondrial genes can cause the respiratory chain to break down. It will be appreciated that the scope of the present disclosure includes transfecting mitochondria with at least one or part of one gene involved in mitochondrial function, in particular at least one or part of the 37 mitochondrial genes to restore or increase the function of the respiratory chain. Any or part of a mitochondrial genome, for example human mitochondrial genome, may be introduced into a host mitochondrion using the methods described herein.

Diseases of the mitochondrial appear to cause the most damage to cells of the brain, heart, liver, skeletal muscles, kidney and the endocrine and respiratory systems. Thus, transfection of mitochondria in these cells and tissues with specific nucleic acids is within the scope of the present disclosure, in particular transfection of mitochondria with nucleic acids encoding mitochondrial-encoded proteins rather than nuclear-encoded proteins. It will be appreciated that the mitochondria can be transfected to express any protein whether naturally present in the mitochondrion or not naturally encoded by mtDNA or nuclear DNA. Depending on which cells are affected, symptoms may include loss of motor control, muscle weakness and pain, gastro-intestinal disorders and swallowing difficulties, poor growth, cardiac disease, liver disease, diabetes, respiratory complications, seizures, visual/hearing problems, lactic acidosis, developmental delays and susceptibility to infection.

Exemplary mtDNA mutations that can be addressed by the present disclosure include but are not limited to: $tRNA^{leu}$-A3243G, A3251G, A3303G, T3250C T3271C and T3394C; $tRNA^{Lys}$-A8344G, G11778A, G8363A, T8356C; ND1-G3460A; ND4-A10750G, G14459A; ND6T14484A; 12S RNA-A1555G; MTTS2-C12258A; ATPase 6-T8993G, T8993C; $tRNA^{Ser}$(UCN)-T7511C; 11778 and 14484, LHON mutations as well as mutations or deletions in ND2, ND3, ND5, cytochrome b, cytochrome oxidase I-III and ATPase 8.
Nuclear Disease:

Muscular Dystrophies, Ellis-van Creveld syndrome, Marfan syndrome, Myotonic dystrophy, Spinal muscular atrophy, Achondroplasia, Amyotrophic lateral sclerosis, Charcot-Marie-Tooth syndrome, Cockayne syndrome, Diastrophic dysplasia, Duchenne muscular dystrophy, Ellis-van Creveld syndrome, Fibrodysplasia ossificans progressive, Alzheimer disease, Angelman syndrome, Epilepsy, Essential tremor, Fragile X syndrome, Friedreich's ataxia, Huntington disease, Niemann-Pick disease, Parkinson disease, Prader-Willi syndrome, Rett syndrome, Spinocerebella atrophy, Williams syndrome, Ataxia telangiectasia, Anemia, sickle cell, Burkitt lymphoma, Gaucher disease, Hemophilia, Leukemia, Paroxysmal nocturnal hemoglobinuria, Porphyria, Thalassemia, Crohn's disease, Alpha-1-antitrypsin deficiency, Cystic fibrosis, Deafness, Pendred syndrome, Glaucoma, Gyrate atrophy of the choroid and retina, Adrenal hyperplasia, Adrenoleukodystrophy, Cockayne syndrome, Long QT syndrome, Immunodeficiency with hyper-IgM, Alport syndrome, Ellis-van Creveld syndrome, Fibrodysplasia ossificans progressive, Waardenburg syndrome, Werner syndrome.
Infectious Disease:

Viral—AIDS, AIDS Related Complex, Chickenpox (Varicella), Common cold, Cytomegalovirus Infection, Colorado tick fever, Dengue fever, Ebola haemorrhagic fever, Epidemic parotitis, Flu, Hand, foot and mouth disease, Hepatitis—Herpes simplex, Herpes zoster, HPV, Influenza, Lassa fever, Measles, Marburg haemorrhagic fever, Infectious mononucleosis, Mumps, Poliomyelitis, Progressive multifocal leukencephalopathy, Rabies, Rubella, SARS, Smallpox (Variola), Viral encephalitis, Viral gastroenteritis, Viral meningitis, Viral pneumonia, West Nile disease—Yellow fever; Bacterial—Anthrax, Bacterial Meningitis, Brucellosis, Bubonic plague, Campylobacteriosis, Cat Scratch Disease, Cholera, Diphtheria, Epidemic Typhus, Gonorrhea, Hansen's Disease, Legionellosis, Leprosy, Leptospirosis, Listeriosis, Lyme Disease, Melioidosis, MRSA infection, Nocardiosis, Pertussis, Pneumococcal pneumonia, Psittacosis, Q fever, Rocky Mountain Spotted Fever or RMSF, Salmonellosis, Scarlet Fever, Shigellosis, Syphilis, Tetanus, Trachoma, Tuberculosis, Tularemia, Typhoid Fever, Typhus, Whooping Cough; Parasitic—African typanosomiasis, Amebiasis, Ascariasis, Babesiosis, Chagas Disease, Clonorchiasis, Cryptosporidiosis, Cysticercosis, Diphyllobothriasis, Dracunculiasis, Echinococcosis, Enterobiasis, Fascioliasis, Fasciolopsiasis, Filariasis, Free-living amebic infection, Giardiasis, Gnathostomiasis, Hymenolepiasis, Isosporiasis, Kala-azar, Leishmaniasis, Malaria, Metagonimiasis, Myiasis, Onchocerciasis, Pediculosis, Pinworm Infection, Scabies, Schistosomiasis, Taeniasis, Toxocariasis, Toxoplasmosis, Trichinellosis, Trichinosis, Trichuriasis, Trypanosomiasis.

Cancers:

Breast and ovarian cancer, Burkitt lymphoma, Chronic myeloid leukemia, Colon cancer, Lung cancer, Malignant melanoma, Multiple endocrine neoplasia, Neurofibromatosis, p53 LieFrauMeni, Pancreatic cancer, Prostate cancer, retinoblastoma, von Hippel-Lindau syndrome, Polycystic kidney disease, Tuberous sclerosis.

Metabolic Disorders:

Adrenoleukodystrophy, Atherosclerosis, Best disease, Gaucher disease, Glucose galactose malabsorption, Gyrate atrophy, Juvenile onset diabetes, Obesity, Paroxysmal nocturnal hemoglobinuria, Phenylketonuria, Refsum disease, Tangier disease, Tay-Sachs disease, Adrenoleukodystrophy, Type 2 Diabetes, Gaucher disease, Hereditary hemochromatosis, Lesch-Nyhan syndrome, Maple syrup urine disease, Menkes syndrome, Niemann-Pick disease, Pancreatic cancer, Prader-Willi syndrome, Porphyria, Refsum disease, Tangier disease, Wilson's disease, Zellweger syndrome progerias, SCID.

Autoimmune Disorders:

Autoimmune polyglandular syndrome, lupus, type I diabetes, scleroderma, multiple sclerosis, Crohn's disease, myasthenia gravis, myositis, antiphospholipid syndrome (APS), uveitis, polymyositis, Raynaud's phenomenon, and demyelinating neuropathies, and rare disorders such as polymyalgia rheumatica, temporal arteritis, Sjogren's syndrome, Bechet's disease, Churg-Strauss syndrome, and Takayasu's arteritis.

Inflammatory Disorders:

Alopecia, Diastrophic dysplasia, Ellis-van Creveld syndrome, Asthma, Arthritis, including osteoarthritis, rheumatoid arthritis, and spondyloarthropathies.

Age-Related Disorders:

Alzheimer Diseases, Parkinson's Disease, Atherosclerosis, Age-Related Macular Degeneration, Age-related Osteoporosis.

The disclosed methods and compositions can also be used to treat, manage, or reduce symptoms associated with aging, in tissue regeneration/regenerative medicine, stem cell transplantation, inducing reversible genetic modifications, expressing dsRNA by the mitochondrial genome, cognitive enhancement, performance enhancement, and cosmetic alterations to human or non-human animal.

One embodiment of the present disclosure provides a method for restoring or increasing respiratory chain function in host cell including administering the disclosed vehicles to a host, wherein the vehicle comprises a polynucleotide, polypeptide, or combination thereof that compensates for the genetic dysfunction, for example that is or encodes a respiratory chain protein or peptide.

Another embodiment of the present disclosure provides a method for restoring or increasing cytochrome oxidase activity in a host including transfecting mitochondria in a cell using the disclosed vehicles, for example a skeletal muscle cell, wherein the vehicle comprises a nucleic acid that encodes cytochrome oxidase or a functional component thereof. A functional component means a part or fragment of the protein or protein complex or subunit that performs a biological function independently or in combination with another protein, fragment, or subunit.

Still another embodiment of the present disclosure provides a method of increasing or restoring β-oxidation in a host including obtaining cells from the host, transfecting an organelle in the cells from the host, by using the disclosed vehicles to deliver proteins involved in β-oxidation spiral and carnitine transport or a nucleic acid encoding such proteins.

Other embodiments of the disclosure are directed to methods of restoring mitochondrial function lost or decreased as a result of point mutations or deletions. For example, KSS, PEO and Pearson, are three diseases that result from a type of mtDNA mutation called a deletion (specific portions of the DNA are missing) or mtDNA depletion (a general shortage of mtDNA). Thus, cells from hosts diagnosed with KSS, PEO, Pearson or similar disease can have their mitochondria transfected using the disclosed vehicles. A vehicle comprising a nucleic acid that compensates for the deletion in the mtDNA causing the diseased state can be used to introduce the nucleic acid into cells. The nucleic acid can be expressed and the protein can then incorporate into the mitochondria and increase or restore mitochondrial function. The transfected cells can be reintroduced in the host. It will be appreciated that the host's cells or other cells can be transfected as described herein and introduced into a host having a dysfunctional organelles, in particular mitochondria.

It will be appreciated by those skilled in the art that the present disclosure encompasses delivering either separately or in combination nucleic acids to the mitochondria that are naturally encoded by mtDNA or nuclear DNA.

The present disclosure also contemplates alleviating the symptoms of mitochondrial diseases by creating cells having transfected and non-transfected mitochondria. Alternatively, all of the mitochondria in a cell can be transfected or replaced.

One embodiment provides a method for compensating for a mtDNA mutation in a host, the method including identifying a host having a mtDNA mutation, obtaining a cell comprising said mtDNA mutation from said host, transfecting a mitochondrion of the host cell using the disclosed vehicles to deliver a nucleic acid that encodes a functional product corresponding to the mtDNA mutation, and introducing said transfected cell into the host. A nucleic acid that encodes a functional product corresponding to the mtDNA mutation means a sequence that produces a protein without the corresponding mutation. For example, if a host cell has an ND4-A10750G mutation, the transfected nucleic acid would encode a wildtype product for the ND4 gene.

Another embodiment provides a method for transfecting a cell with a target polynucleotide comprising contacting the cell with the disclosed vehicles, wherein the cargo delivery vehicle comprises the target polynucleotide.

Still another embodiment provides a method for transfecting a cell or mitochondrion with a target polynucleotide comprising, contacting the cell or mitochondrion with a recombinant mitochondrion under conditions that promote mitochondrial fusion, wherein the recombinant mitochondrion comprises the target polynucleotide. The target polynucleotide encodes or is an anti-sense nucleic acid, siRNA, microRNA or a polypeptide. In one embodiment, mitochondrial fusion is facilitated by fusion proteins such as Mfn1, Mfn2, compounds such as GTP, creatine, ATP, inhibitors of mitochondrial fission such as siRNAs to Drp1, and hFis1.

A recombinant mitochondrion is a mitochondrion that is transfected with a nucleic acid originating from a source other than the mitochondrion or is a mitochondrion that has had its genome altered by inserting or deleting a nucleic acid into the mitochondrion or the genome of the mitochondrion. Typically, the recombinant mitochondrion expresses an exogenous nucleic acid. The nucleic acid can encode a polypeptide that compensates for a genetic defect in the mitochondrion or nucleus of a cell.

IV. Fusion Proteins

One embodiment provides a fusion protein comprising an amino acid sequence according to SEQ ID NO:1 or a fragment thereof operably linked to a reporter and, optionally a targeting polypeptide. Suitable reporters include fluorescent proteins, luminescent proteins, or a combination thereof. An exemplary reporter is Green Fluorescent Protein or a variant thereof. A suitable targeting polypeptide includes the mitochondrial matrix localization signal from malate dehydrogenase. It will be appreciated that other mitochondrial targeting polypeptides can be used. The fusion protein is useful for tracking movement of Cav1 through the vesicular transport mechanism of a cell.

In other embodiments, the disclosed fusion proteins can be incorporated into the synthetic delivery vehicles.

Another embodiment provides a vector comprising a nucleic acid encoding the disclosed fusion proteins. Suitable vectors include but are not limited to plasmids. The vector optionally contains sufficient control sequences for expressing the nucleic acid in a cell. For example, the vector may include a promoter, typically an inducible promoter. Suitable promoters for expression in *E. coli*, for example include T7, T5, Lac promoters. Depending on the types of cells used, other promoters could be used including, but not limited to adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the β-actin promoter; and human growth hormone promoters.

V. Kits

Another embodiment provides a kit comprising one or more of the disclosed cargo delivery vehicles, fusion proteins, or one or more nucleic acids encoding one or more of the disclosed fusion proteins. The kit optionally includes a buffered carrier solution to buffer the pH and/or salt concentration of the solution containing the vehicles. Another embodiment provides a kit including a cell expressing one or more of the disclosed fusion proteins. Buffered solutions and cell culture media may also be included in the kit.

Another embodiment provides reagents for producing the disclosed synthetic vehicle. Suitable reagents include lipids, CAV1 protein or polypeptides, solvents, and buffers. The lipids can be supplied dried or in solvent.

Administration

The delivery vehicles provided herein may be administered in a physiologically acceptable carrier to a host. A typical host includes mammals, preferably, a human. Preferred methods of administration include systemic or direct administration to a cell. The vesicle compositions can be administered to a cell or patient, as is generally known in the art for gene therapy applications. In gene therapy applications, the compositions are introduced into cells in order to transfect an organelle.

"Gene therapy" includes both conventional gene therapy where a lasting effect is achieved by a single treatment, and the administration of gene therapeutic agents, which involves the one time or repeated administration of a therapeutically effective DNA or RNA.

The vesicle compositions can be combined in admixture with a pharmaceutically acceptable carrier vehicle. Therapeutic formulations are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween™, Pluronics or PEG.

The compositions of the present disclosure can be administered parenterally. As used herein, "parenteral administration" is characterized by administering a pharmaceutical composition through a physical breach of a subject's tissue. Pharmaceutical administration includes administering by injection, through a surgical incision, or through a tissue-penetrating non-surgical wound, and the like. In particular, parenteral administration includes subcutaneous, intraperitoneal, intravenous, intraarterial, intramuscular, intrasternal injection, and kidney dialytic infusion techniques.

Parenteral formulations can include the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Parenteral administration formulations include suspensions, solutions, emulsions in oily or aqueous vehicles, pastes, reconsitutable dry (i.e. powder or granular) formulations, and implantable sustained-release or biodegradable formulations. Such formulations may also include one or more additional ingredients including suspending, stabilizing, or dispersing agents. Parenteral formulations may be prepared, packaged, or sold in the form of a sterile injectable aqueous or oily suspension or solution. Parenteral formulations may also include dispersing agents, wetting agents, or suspending agents described herein. Methods for preparing these types of formulations are known. Sterile injectable formulations may be prepared using non-toxic parenterally-acceptable diluents or solvents, such as water, 1,3-butane diol, Ringer's solution, isotonic sodium chloride solution, and fixed oils such as synthetic monoglycerides or diglycerides. Other parentally-administrable formulations include microcrystalline forms, liposomal preparations, and biodegradable polymer systems. Compositions for sustained release or implantation may include pharmaceutically acceptable polymeric or hydrophobic materials such as emulsions, ion exchange resins, sparingly soluble polymers, and sparingly soluble salts.

Pharmaceutical compositions may be prepared, packaged, or sold in a buccal formulation. Such formulations may be in the form of tablets, powders, aerosols, atomized solutions, suspensions, or lozenges made using known methods, and may contain from about 0.1% to about 20% (w/w) active ingredient with the balance of the formulation containing an orally dissolvable or degradable composition and/or one or more additional ingredients as described herein. Preferably, powdered or aerosolized formulations have an average particle or droplet size ranging from about 0.1 nanometers to about 200 nanometers when dispersed.

As used herein, "additional ingredients" include one or more of the following: excipients, surface active agents, dispersing agents, inert diluents, granulating agents, disintegrating agents, binding agents, lubricating agents, sweetening agents, flavoring agents, coloring agents, preservatives, physiologically degradable compositions (e.g., gelatin), aqueous vehicles, aqueous solvents, oily vehicles and oily solvents, suspending agents, dispersing agents, wetting agents, emulsifying agents, demulcents, buffers, salts, thickening agents, fillers, emulsifying agents, antioxidants, antibiotics, antifungal agents, stabilizing agents, and pharmaceutically acceptable polymeric or hydrophobic materials. Other "additional ingredients" which may be included in the pharmaceutical compositions are known. Suitable additional ingredients are described in Remington's Pharmaceutical Sciences, Mack Publishing Co., Genaro, ed., Easton, Pa. (1985).

Dosages and desired concentrations modified vectors disclosed herein in pharmaceutical compositions of the present disclosure may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" n Toxicokinetics and New Drug Development, Yacobi et al., Eds., Pergamon Press, New York 1989, pp. 42-96.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally in its sense including "and/or" unless the content clearly dictates otherwise.

EXAMPLES

Materials and Methods

The following exemplary methods and materials were used to provide the data presented in the accompanying working examples.

DNA Constructs:

MLS-Cav1-GFP was generated by PCR. Briefly, primers incorporating the mitochondrial targeting signal of mMDH were generated and the Cav1 cDNA was amplified from an IMAGE clone. The MLS-Cav1 PCR product was topoisomerase-TA cloned into pTOPOTA-CTerminal GFP (Invitrogen). The resulting clone was verified by sequencing. pDsRed2-Mito was purchased from Clontech.

siRNA:

Double stranded siRNAs to Cav1, Mfn1 and hFis1 were purchased from Qiagen and contained terminal dUdT overhangs. The siRNA sequences against Cav1 were 5'-AGACGAGCUGAGCGAGAAGCA-3' (SEQ ID NO:8) (sense) and 5'-CUUCUCGCUCAGCUCGUCUGC-3' (SEQ ID NO:9) (antisense). The siRNA sequences against hFis1 were 5'-GTATAATGATGATATTTGTAA-3' (SEQ ID NO:10) (sense) and 5'-TTACGGATGTCATCATTGTAC-3' (antisense). The siRNA sequences against Mfn1 were 5'-AAGGGGATTACTGCAATCTTT-3' (SEQ ID NO:11) (sense) and 5'-AAAGATTGCAGTAATCCCCTT-3' (SEQ ID NO:12) (antisense).

Cell Culture:

SH-Sy5y neuroblastoma cells were propagated in complete DMEM (Gibco), trypsinized, counted and plated onto Matek coverslipped dishes at 50% confluence.

Transfection:

siRNAs were transfected into cells with use of Oligofectamine transfection reagent (Invitrogen) as proscribed. For MLS-Cav1-GFP transfection SH-Sy5y cells. Lipofectamine 2000 transfection reagent was used (Invitrogen) according to manufacturer's instructions.

Immunostaining:

After at least 24 h of siRNA transfection, cells were incubated with MitoTracker Red for 10 min at 37° C., washed three times with Hanks Buffered Saline (pH 7.4) and fixed for 10 min at 37° C. in ice-cold methanol. After additional washes with PBS, the cells were permeabilized with 0.1% triton in PBS for 10 min. After blocking with 3% BSA-0.2% Tween-20 for 1 h at 37° C., the cells were incubated with mouse monoclonal anti-Cav1 (UpState) antibody or anti-Mfn1 (Santa Cruz) antibody in BSA blocking solution for 1 h at 37° C. and washed four times with PBS. The cells were incubated with Alexa Fluor 488 or 568 antimouse IgG (Molecular Probes) secondary antibody for 1 h at 37° C. and washed four times in PBS. Cells were coverslipped with Vectashield (Vector Labs).

Confocal Microscopy:

Single plane confocal images of MLS-Cav1-GFP, pDSRed2-Mito or immunostained cells were collected using an Olympus Confocal Laser Scanning System mounted on an Olympus IX70 microscope. Twenty-four-bit TIFF confocal images were converted to 16-bit RGB bitmap images without altering image intensity or color using Adobe Photoshop.

Example 1

Lipid Rafts Colocalize with Mitochondria

To begin to discern the relationship between mitochondria and lipid rafts, cells were incubated with the lipid raft binding beta subunit of cholera toxin covalently linked with FITS (CTB-FITC). When stained with Mitotracker Red, cells possessed regions of colocalization. This colocalization was also seen upon the addition of vector protein/DNA complexes, implying that there is a subpopulation of lipid rafts that colocalize with mitochondria and that this colocalization can be seen upon certain stimuli. The integration of lipid rafts with mitochondrial membranes suggests that a fusion machinery might exist to support this interaction.

Since mitochondria fuse with other mitochondria, the same fusion machinery may mediate lipid raft fusion with mitochondria. To begin to test the hypothesis, SH-SY5Y cells were initially stained with anti-caveolin and anti-Mfn1 (Mitofusin 1) antibodies. In the basal state, there appeared to be regions where both proteins were colocalized. Using siRNA to achieve knockdown of Cav1, the question of whether lacking a component of lipid rafts would prevent uptake of vector protein/DNA complexes into cells was addressed. Cells lacking Cav1 expression and incubated with vector protein/Alexa488-DNA complexes produced uptake of protein/DNA complexes into the cytosol, indicating that caveolae are important but not necessary for uptake. Furthermore, cells lacking Cav1 produced a pronounced change in mitochondrial morphology showing reduced membrane potential and spherical as opposed to tubular mitochondria suggesting that Cav1 is a regulator of mitochondrial morphology.

To test whether the mitochondrial fusion machinery was involved in uptake of the vector protein-DNA complexes, the expression of Mfn1 was knocked down and cells were incubated with vector-protein/DNA complexes. Immunostaining for the complexes showed uptake into the cytosol suggesting Mfn1 was not involved in lipid raft internalization from the plasma membrane. This was not surprising given the strictly mitochondrial localization of Mfn1.

Example 2

MLS-Cav1-GFP Translocates to the Plasma Membrane

To better understand the dynamics of mitochondrial Cav-1, a mitochondrially-targeted caveolin1 fused to GFP using the mitochondrial matrix localization signal from malate dehydrogenase (MLS-Cav1-GFP) was generated. Transfection of this construct into SH-SY5Y cells produced both a cytosolic localization as well as plasma membrane localization, implying that once imported into mitochondria, the MLS-Cav1-GFP was able to translocate to the plasma membrane.

Since many mitochondrial proteins are found in lipid rafts on the plasma membrane including ATPase subunits, VDAC, mtDNA encoded ND2, etc., the mitochondrial fission machinery may be involved in pinching lipid rafts containing Cav-1 from mitochondrial membranes where the lipid raft is free to associate with other cellular membranes such as the plasma membrane. To assess this question, cells co-transfected with the MLS-Cav1-GFP construct as well as pDsRed2-Mito (Clontech) were imaged at 24, 36, and 48 hours post-transfection. At 24 hours, red fluorescing mitochondria (mito-RFP) possessed regions of green fluorescing cav-1 expression mostly on the periphery suggesting association with the mitochondrial outer membrane, though matrix localization was also apparent.

Since RNAi mediated knockdown of Cav1 produced altered mitochondrial morphology, siRNA against hFis1 (Stojanovski et al., 2004), a member of the mitochondrial fission machinery, was utilized on cells co-transfected with MLS-Cav1-GFP and DsRed2-Mito. These cells had a total suppression of Cav1 translocation from mitochondria suggesting mitochondrial fission in release of lipid rafts from mitochondria.

Example 3

Uptake of Whole Mitochondria into Cells

Lipid rafts on the plasma membrane are known to interact with the extracellular milieu and are involved in the endocytosis of large complexes, including viruses and bacteria. Previously, Clark and Shay (1982) had shown uptake of whole mitochondria into cells as a means of transforming mitochondria in situ and rescuing a rho zero phenotype (Clark and Shay, 1982). To ascertain whether or not mitochondria and their constituents are transferable, cells expressing MLS-Cav1-GFP were co-cultured with cells transfected with DsRed2-Mito. Cells were transfected in separate dishes with either the MLS-Cav1-GFP or DsRed2-Mito constructs and allowed to recover for 24 hours. The cells were then collected, washed, and plated on the same culture dish. Negative controls included dummy transfected cells that were plated in the presence of both DNA constructs. After 24 hours, co-cultured cells were visualized under confocal for regions of yellow fluorescence, indicating that the mitochondria of one cell type (e.g., DsRed2-Mito) had invaded the mitochondria of another (MLS-Cav1-GFP). Remarkably, co-culturing produced regions of yellow that were verified with antibody staining whereas control cells failed to show any fluorescence. Though at this time cell fusion cannot be ruled out, the literature suggests cell fusion to be a rare event and insufficient to explain our findings.

Caveolin Protein Sequence Sequence.

Accession No. [gi:38516] (SEQ ID NO:1)
msggkyvdse ghlytvpire qgniykpnnk amadelsekq vydahtkeid lvnrdpkhln ddvvkidfed viaepegths fhgiwkasft tftvtkywfy rllsalfgip maliwgiyfa ilsflhiwav vpciksflie iqctsrvysi yvhtvcdplf eavgkifsnv rinlqkei

TABLE 2

Localization Signals for Targeting to the Mitochondria.
(verified using Mitochondrial Project MITOP Database--
http://mips.gsf.de/proj/medgen/mitop/)

| MITOP Designation (Accession No.) | Gene Name | Gene Name Full |
|---|---|---|
| 106092 (NP633590) | Etfa | electron transfer flavoprotein alpha chain precursor - mouse |
| 106098 (Q9DCW4) | Etfb | electron transfer flavoprotein beta chain - mouse |
| 107450 (NP000099) | Dld | dihydrolipoamide dehydrogenase precursor - human |
| 87979 (NP067274) | Ak3 | nucleoside-triphosphate--adenylate kinase 3 - mouse |
| 88529 (NP080720) | Cs | citrate synthase, mitochondrial |
| 891996 (AA031763) | Cps1 | carbamoyl-phosphate synthetase 1 |
| 97045 (NP032641) | Mod2 | malic enzyme complex, mitochondrial - mouse |
| 97499 (AAH49802) | Pcca | propionyl-CoA carboxylase alpha chain precursor - mouse |
| A27883 (NP000273) | PCCA | propionyl-CoA carboxylase alpha chain precursor |
| A28053 NP031647 | Cbr2 | carbonyl reductase (NADPH) - mouse |
| A29881 (XP331748) | mpp-2 | Mitochondrial processing peptidase beta subunit precursor (beta-mpp) (ubiquinol-cytochrome c reductase complexcore protein 1) |
| A30605 (NP000008) | ACADS | acyl-CoA dehydrogenease precursor, short-chain-specific |
| A31998 (WP000117) | ETFA | electron transfer flavoprotein alpha chain precursor |
| A32422 | DBT | dihydrolipoamide S-(2-methylpropanoyl)transferase precursor |
| A32800 (NP002147) | HSPD1 | heat shock protein 60 precursor |
| A36442 (XP326125) | mpp-1 | Mitochondrial processing peptidase alpha chain precursor |
| A37033 (NP002216) | IVD | isovaleryl-CoA dehydrogenase precursor |
| A37157 (NP898871) | BCKD | 3-methyl-2-oxobutanoate dehydrogenase (lipoamide E1-beta chain precursor |
| A38234 | OGDH | oxoglutarate dehydrogenase (lipoamide) precursor |
| A39503 (NP002387) | ME2 | malate dehydrogenase (NAD+) precursor, mitochondrial |
| A40487 (NP004101) | FDXR | Ferredoxin--NADP+ reductase, long from, precursor |
| A40559 (NP001599) | ACADL | long-chain-acyl-CoA dehydrogenase (LCAD) |

TABLE 2-continued

Localization Signals for Targeting to the Mitochondria.
(verified using Mitochondrial Project MITOP Database--
http://mips.gsf.de/proj/medgen/mitop/)

| MITOP Designation (Accession No.) | Gene Name | Gene Name Full |
|---|---|---|
| A40872 | ALDH5 | aldehyde dehydrogenase (NAD+) 5 precursor, mitochondrial |
| A41581 (NP005720) | CYP3 | peptidylprolyl isomerase 3 precursor |
| A42224 (P22572) | arg-2 | Carbamoyl-phosphate synthase, arginine-specific, small chain precursor (arginine-specific carbamoyl - phosphate synthetase, glutamine chain) (cps-a) |
| A42845 | BDH | D-beta-hydroxybutyrate dehydrogenase precursor (3-hydroxybutyrate dehydrogenase) (fragment) |
| A45470 (AAP88794) | HMGC | hydroxymethylglutaryl-CoA lyase |
| A47255 (AAH55030) | Pcx | pyruvate carboxylase |
| A53020 (AAH53661) | PCCB | propinoyl-CoA carboxylase beta chain precursor |
| A53719 (NP036216) | GLUDP | glutamate dehydrogenase (NAD(P)+) 2 precursor |
| A55075 (NP032329) | HspE1 | chaperonin-10 |
| A55680 (NP001600) | ACADS | short/branched chain acyl-CoA dehydrogenase precursor |
| A55723 (P42126) | DCI | dodecenoyl-CoA Delta-isomerase precursor, mitochondrial |
| A55724 (NP031408) | Acadm | Acyl-CoA dehydrogenase, medium-chain specific precursor (MCAD) |
| AA227572 (NM201263) | WARS2 | tryptophanyl-tRNA synthetase 2 (mitochondrail) - human |
| AB029948 (NP060297) | SerRS | mitochondrial seryl-tRNA synthetase (cDNA FLJ20450 FIS, CLONE KAT0560) - human |
| ACDL_MOUSE (AAH27412) | Acadl | Acyl-CoA dehydrogenase, long-chain specific precursor (LCAD) |
| AF047042 (AAC25560) | CS | citrate synthase, mitochondrial |
| AF097441 (NP006558) | FARS1 | phenylalanine-tRNA synthetase (FARS1) mRNA, nuclear gene encoding mitochondrial protein - human |
| ATPO_HUMAN (NP001688) | ATP5O | ATP synthase oligomycin sensitivity conferral protein precursor, mitochondrial |
| AXHU (AAP35327) | FDX1 | adrenodoxin precursor |
| CCHU (NP061820) | HCS | cytochrome c |
| CCNC (CAA29050) | cyc-1 | Cytochrome c |
| CE06620 (NP056155) | — | Probable leucyl-tRNA synthetase mitochondrial |
| CE09597 (AAG31658) | — | Pyruvate dehydrogenase (E2) dihydrolipoamide acetyltransferase |
| CH10_MOUSE (NP032329) | Hspe1 | 10 KD heat shock protein, mitochondrial (hsp10) (10K chaperonin) mouse |
| CH60_CAEEL (NP467429) | hsp60 | Chaperonin homolog hsp60 precursor (heat shock protein 60) (hsp-60) |
| DEHUE2 (NP000681) | ALDH2 | aldehyde dehydrogenase (NAD+) 2 precursor, mitochondrial |
| DEHUE (NP005262) | GLUD1 | glutamate dehydrogenase (NAD(P)+) precursor |
| DEHULP (NP000099) | DLD | dihydrolipoamide dehydrogenase precursor |
| DEHUPA (NP000275) | PDHA1 | pyruvate dehydrogenase (lipoamide) alpha chain precursor |
| DEHUPB (AAH00439) | PDHB | pyruvate dehydrogenase (lipoamide) beta chain precursor |
| DEHUPT (NP005381) | PDHA2 | pyruvate dehydrogenase (lipoamide) alpha chain precursor, testis-specific (E1) |
| DEHUXA (NP000700) | BCKDH | 3-methyl-2-oxobutanoate dehydrogenase (lipoamide) alpha chain precursor |
| DEMSMM (P08249) | Mor1 | malate dehydrogenase precursor, mitochondrial |
| DSHUN | SOD2 | superoxide dismutase (Mn) precursor |
| ECHM_HUMAN (NP004083) | ECHS1 | enoyl-CoA hydratase, mitochondrial (short chain enoyl-CoA hydratase (SCEH)) |
| GABT_HUMAN (JC4022) | ABAT | 4-aminobutyrate aminotransferase, mitochondrial precursor (gamma-amino-N-butyrate-transaminase) (GABA transaminase) |
| GCDH_HUMAN (AAP35352) | GCDH | glutaryl-CoA dehydrogenase precursor (GCD) - human |
| GCDH_MOUSE (NP032123) | Gcdh | Glutaryl-CoA dehydrogenase precursor (GCD) - mouse |
| HCD1_CAEEL (NP499075) | — | Probable 3-hydroxyacyl-CoA dehydrogenase F54C8.1 |
| HCD2_CAEEL (NP509584) | — | Probable 3-hydroxyacyl-CoA dehydrogenase B0272.3 |
| HHMS60 (NP034607) | Hsp60 | heat shock protein 60 precursor |
| HMGL_MOUSE (AAB27965) | Hmgcl | hydroxymethylglutaryl-CoA lyase precursor (HG-CoA lyase) (HL) (3-hydroxy-3-methylglutarate-CoA lyase) |
| I48884 (AAC52130) | — | 2-oxoglutarate dehydrogenase E1 component (fragment) |
| I48966 (AAH05476) | Aldh2 | aldehyde dehydrogenase (NAD+) 2 precursor, mitochondrial |
| I49605 | Acads | Acyl-CoA dehydrogenase, short-chain specific precursor (SCAD) (butyryl- CoA dehydrogenase) |
| I52240 (NP000007) | ACAD | acyl-CoA dehydrogenase precursor, medium-chain-specific |
| I55465 (AAH39158) | PDK1 | pyruvate dehydrogenase kinase isoform 1 - human |
| I57023 (DSHUN) | Sod2 | superoxide dismutase (Mn) precursor |
| I70159 (AAC42010) | PDK2 | pyruvate dehydrogenase kinase isoform 2 - human |
| I70160 (NP005382) | PDK3 | pyruvate dehydrogenase kinase isoform 3 - human |
| JC2108 (AAA56664) | HADH | long-chain-fatty-acid beta-oxidation multienzyme complex alpha chain precursor, mitochondrial |
| JC2109 (NP000174) | HADH | long-chain-fatty-acid beta-oxidation multienzyme complex beta chain precursor, mitochondrial |
| JC2460 (AAH11617) | PC | pyruvate carboxylase precursor |
| JC4879 (NP005318) | SCHAD | 3-hydroxyacyl-CoA dehydrogenase, short chain-specific, precursor |
| KIHUA3 (AAH16180) | AK3 | nucleoside-triphosphate--adenylate kinase 3 |
| M2GD_HUMAN (AAF21941) | DMGD | dimethylglycine dehydrogenase, mitochondrial precursor (ME2GLYDH) - human |
| MDHM_HUMA (AAH01917) | MDH2 | malate dehydrogenase mitochondrial precursor (fragment) |
| O75439 | PMPC | mitochondrial processing peptidase beta subunit precursor (beta-MPP) (P-52) |
| ODO1_MOUSE (AAC52130) | Ogdh | 2-oxoglutarate dehydrogenase E1 component (alpha-ketoglutarate dehydrogenase) (fragment) |

TABLE 2-continued

Localization Signals for Targeting to the Mitochondria.
(verified using Mitochondrial Project MITOP Database--
http://mips.gsf.de/proj/medgen/mitop/)

| MITOP Designation (Accession No.) | Gene Name | Gene Name Full |
|---|---|---|
| ODPA_CAEEL (NP495693) | — | Probable pyruvate dehydrogenase E1 component, alpha subunit precursor (PDHEI-a) |
| OWHU (NP000522) | OTC | ornithine carbamoyltransferase precursor |
| OWMS (CAA30121) | Otc | ornithine carbamoyltransferase precursor |
| P21549 (NP000021) | AGXT | alanine--glyoxylate aminotransferase |
| PUT2_HUMAN (NP733844) | ALDH4 | Delta-1-pyrroline-5-carboxylate dehydrogenase precursor (P5C dehydrogenase) |
| Q0140 (NP009320) | VAR1 | VAR1 - mitochondrial ribosomal protein |
| Q10713 (NP055975) | KIAA0123 | mitochondrial processing peptidase alpha subunit precursor (alpha-MPP) (P-55) (HA1523) |
| Q16654 (NP002603) | PDK4 | pyruvate dehydrogenase kinase isoform 4 - human |
| ROHU (CAA42060) | TST | thiosulfate sulfurtransferase |
| S01174 (NP034455) | Got2 | aspartate transaminase precursor, mitochondrial |
| S08680 (NP032676) | Mut | methylmalonyl-CoA mutase alpha chain precursor |
| S13025 (CAA39695) | nuo-40 | NADH dehydrogenase (ubiquinone) 40K chain |
| S13048 (P19974) | cyt | cytochrome c |
| S16239 (AAH57347) | Glud | glutamate dehydrogenase (NAD(P)+) precursor |
| S23506 (NP032836) | Pdhal | pyruvate dehydrogenase (lipoamide) |
| S25665 (CAA32052) | DLAT_h | dihydrolipoamide S-acetyltransferase heart - human (fragment) |
| S26984 (P33540) | — | probable DNA-directed RNA polymerase - mitochondrion plasmid maranhar (SGC3) |
| S32482 (NP001976) | ETFB | electron transfer flavoprotein beta chain |
| S38770 (P42125) | Dci | 3,2-trans-enoyl-CoA isomerase, mitochondrial precursor (dodecenoyl-CoA delta-isomerase) |
| S39807 | Bckdhb | 3-methyl-2-oxobutanoate dehydrogenase (lipoamide) beta chain |
| S40622 (NP000246) | MUT | methylmalonyl-CoA mutase precursror (MCM) |
| S41006 (CAE65137) | — | hypothetical protein 105 g 5.6 |
| S41563 | cit-1 | citrate (si)-synthase, mitochondrial |
| S42366 | PRSS15 | Lon proteinase homolog |
| S42370 (NP499264) | — | citrate synthase homolog |
| S47532 (NP002148) | HSPE1 | heat shock protein 10 |
| S53351 (NP006671) | ME2.1 | malate dehydrogenase (oxaloacetate-decarboxylating) (NADP+) precursor, mitochondrial |
| S60028 (NP032023) | Fdxr | ferredoxin--NADP+ reductase precursor |
| S65760 (NP034152) | Dbt | dihydrolipoamide transacylase precursor |
| S71881 (NP031559) | Bckdha | branched chain alpha-ketoacid dehydrogenase chain E1-alpha precursor |
| SCOT_HUMA (NP000427) | OXCT | Succinyl-CoA:3-ketoacid-coenzyme A transferase precursor (succinyl CoA:3- oxoacid CoA-transferase) (OXCT) |
| SODM_CAEEL (NP492290) | sod-2 | Superoxide dismutase precursor (Mn) |
| SODN_CAEEL (NP510764) | sod-3 | Superoxide dismutase precursor (Mn) |
| SYHUAE | ALAS2 | 5-aminolevulinate synthase 2 |
| SYHUAL (NP000679) | ALAS1 | 5-aminolevulinate synthase 1 precursor |
| SYLM_HUMAN (NP056155) | KIAA0028 | Probable leucyl-tRNA synthetase, mitochondrial precursor (Leucine--tRNA ligase) (Leurs) (KIAA0028) |
| SYMSAL | Alas2 | 5-aminolevulinate synthase mitochondrial precursor (erythroid-specific) (ALAS-E) |
| SYNCLM (XP323115) | leu-5 | leucine--tRNA ligase precursor, mitochondrial |
| SYNCYT | cyt-18 | tyrosine--tRNA ligase precursor, mitochondrial |
| SYWM_CAEEL (T15761) | — | Probable tryptophanyl-tRNA synthetase, mitochondrial (tryptophan-- tRNA ligase) (TRPRS) |
| THTR_MOUSE (NP033463) | Tst | thiosulfate sulfurtransferase |
| U80034 (NP005923) | MIPEP | mitochondrial intermediate peptidase |
| U82328 (NP003468) | PDX1 | pyruvate dehydrogenase complex protein X subunit precursor |
| XNHUDM (NP002071) | GOT2 | aspartate transaminase precursor, mitochondrial |
| XNHUO (NP000265) | OAT | ornithine--oxo-acid transaminase precursor |
| XNHUSP (NP000021) | AGXT | serine--pyruvate aminotransferase (SPT) (alanine--glyoxylate aminotransferase) (AGT) |
| XNMSO (AAH08119) | Oat | ornithine--oxo-acid transminase precursor |
| XXHU | DLAT | dihydrolipoamide S-acetyltransferase precursor (fragment) |
| YAL044c (P39726) | GCV3 | GCV3 - glycine decarboxylase, subunit H |
| YBL022c (NP009531) | PIM1 | PIM1 - ATP-dependent protease, mitochondrial |
| YBL038w (NP009515) | MRPL16 | MRPL16 - ribosomal protein of the large subunit, mitochondrial |
| YBL080c (NP009473) | PET112 | PET112 - required to maintain rho + mitochondrial DNA |
| YBL090w (NP009463) | MRP21 | MRP21 - Mitochondrial ribosomal protein |
| YBR120c (NP009678) | CBP6 | CBP6 - apo-cytochrome B pre-mRNA processing protein |
| YBR122c (CAA55624) | MRPL36 | MRPL36 - ribosomal protein YmL36 precursor, mitochondrial |
| YBR146w (NP009704) | MRPS9 | MRPS9 - ribosomal protein S9 precursor, mitochondrial |
| YBR221c (NP009780) | PDB1 | PDB1 - pyruvate dehydrogenase (lipoamide) beta chain precursor |
| YBR227c (NP009786) | MCX1 | MCX1 - ClpX homologue in mitochondria |
| YBR251w (NP009810) | MRPS5 | MRPS5 - ribosomal protein S5, mitochondrial |
| YBR268w (NP009827) | MRPL37 | MRPL37 - ribosomal protein YmL37, mitochondrial |
| YBR282w (NP009841) | MRPL27 | MRPL27 - ribosomal protein YmL27, precursor, mitochondrial |
| YCR003w (NP009929) | MRPL32 | MRPL32 - ribosomal protein YmL32, mitochondrial |
| YCR024c (NP009953) | — | asn-tRNA synthetase, mitochondrial |
| YCR028c-a (NP009958) | RIM1 | RIM1 - ssDNA-binding protein, mitochondrial |
| YCR046c (NP009975) | IMG1 | IMG1 - ribosomal protein, mitochondrial |
| YDL202w (NP010079) | MRPL11 | MRPL11 - ribosomal protein of the large subunit, mitochondrial |

TABLE 2-continued

Localization Signals for Targeting to the Mitochondria.
(verified using Mitochondrial Project MITOP Database--
http://mips.gsf.de/proj/medgen/mitop/)

| MITOP Designation (Accession No.) | Gene Name | Gene Name Full |
|---|---|---|
| YDR148c (NP010432) | KGD2 | KGD2 - 2-oxoglutarate dehydrogenase complex E2 component |
| YDR194c (NP010480) | MSS116 | MSS116 - RNA helicase of the DEAD box family, mitochondrial |
| YDR462w (NP010750) | MRPL28 | MRPL28 - ribosomal protein of the large subunit (YmL28), mitochondrial |
| YFL018c (NP116635) | LPD1 | LPD1 - dihydrolipoamide dehydrogenase precursor |
| YGR244c (NP011760) | LSC2 | succinate-CoA ligase beta subunit |
| YHR008c (NP011872) | SOD2 | SOD2 - superoxide dismutase (Mn) precursor, mitochondrial |
| YIL070c (NP012194) | MAM33 | MAM33 - mitochondrial acidic matrix protein |
| YJL096w (CAA89390) | MRPL49 | MRPL49 - ribosomal protein YmL49, mitochondrial |
| YJR113c (NP012647) | RSM7 | RSM7 - similarity to bacterial, chloroplast and mitochondrial ribosomal protein S7 |
| YKL040c (NP012884) | NFU1 | NFU1 - iron homeostasis |
| YLL027w (NP013073) | ISA1 | ISA1 - mitochondrial protein required for normal iron metabolism |
| YLR059c (NP013160) | REX2 | REX2 - putative 3'-5' exonuclease |
| YML110c (NP013597) | COQ5 | COQ5 - ubiquinone biosynthesis, methyltransferase |
| YMR062c (NP013778) | ECM40 | ECM40 - acetylornithine acetyltransferase |
| YMR072w (NP013788) | ABF2 | ABF2 - high mobility group protein |
| YOL095c (NP014546) | HMI1 | HMI1 - mitochondrial DNA helicase |
| YOR040w (NP014683) | GLO4 | GLO4 - glyoxalase II (hydroxyacylglutathione hydrolase) |
| YOR142w (NP014785) | LSC1 | LSC1 - succinate-CoA ligase alpha subunit |
| YPL118w (NP015207) | MRP51 | MRP51 - srtong similarity to S. kluyveri hypothetical protein |
| YPL135w (NP015190) | ISU1 | ISU1 - protein with similarity to iron-sulfur cluster nitrogen fixation proteins |
| YPL252c (NP015071) | YAH1 | YAH1 - similarity to adrenodoxin and ferrodoxin |
| YPL262w (NP015061) | FUM1 | FUM1 - fumarate hydratase |
| YPR047w (CAA89167) | MSF1 | MSF1 - phenylalanine--tRNA ligase alpha chain, mitochondrial |
| YPR067w (NP015392) | ISA2 | ISA2 - mitochondrial protein required for iron metabolism |

TABLE 3

Localization Signals for Targeting to the Chloroplast:

| Designation (Accession No.) | Description |
|---|---|
| CA782533 | Transit peptide domain of the apicoblast ribosomal protein S9 |
| P27456 (CAA62482) | Pea glutathione reductase (GR) signal peptide |
| BAB91333 | $NH_2$-terminus of Cr-RSH encoding a putative guanosine 3',5'-bispyrophosphate (ppGpp) synthase-degradase |
| CAB42546 | 14-3-3 proteins |
| AAC64139 AAC64109 AAD01509 | Chloroplast signal recognition particle including cpSRP54, cpSRP43 subunits or a fragment thereof |
| PWSPG, FESP1, P00221, P05435, BAA37170, BAA37171, AAA81472 | Chloroplast transit peptides |
| X52428 (CAA36675) | AtOEP7, in particular the transmembrane domain (TMD) and its C-terminal neighboring seven-amino acid region (see Lee YJ, Plant Cell 2001 Oct; 13(10): 2175-90) |
| CA757092, CA755666 | THI1 N-terminal chloroplastic transit peptide, in particular 4 to 27 residues |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

What is claimed is:

1. A synthetic vesicle comprising:
artificial lipid rafts comprising one or more lipids in combination with one or more fusion proteins comprising a polypeptide having an amino acid sequence according to SEQ ID NO:1 fused to a targeting signal, wherein the one or more lipids and fusion proteins are present in an amount effective to form artificial lipid rafts in the synthetic vesicle, wherein the synthetic vesicle is multilamellar.

2. The vesicle of claim 1, wherein the targeting signal is selected from the group consisting of a nuclear localization signal, mitochondrial localization signal, chloroplast localization signal, or a combination thereof.

3. A synthetic vesicle comprising:
(a) artificial lipid rafts comprising:
one or more lipids in combination with one or more polypeptides having an amino acid sequence according to SEQ ID NO:1 wherein the one or more lipids and one or more polypeptides are present in an amount effective to form artificial lipid rafts in the synthetic vesicle; and
(b) a mitochondrial targeting signal.

4. The vesicle of claim 3, wherein the one or more lipids comprise cationic lipids.

5. The vesicle of claim 3, wherein the one or more lipids comprise phosphatidylcholine, phosphatidylserine, phosphatidylethanolamine, phosphatidyl glycerol, sphingomyelin, cholesterol, ioleoylphosphatidylethanolamine, dioleoy-dimethylammonium chloride (DODAC), cholesteryl hemisuccinate, 3-[N—(N',N'-dimethylaminoethane)-carbamoyl]cholesterol hydrochloride (DC-Chol), dioleoylphosphatidic acid (DOPA), 1,2-Dioleoyl-sn-Glycero-3-Phosphoethanolamine (DOPE), Dimethyldioctadecylammonium Bromide (DDAB), 1,2-Dioleoyl-3-Trimethylammonium-Propane (DOTAP), 1,2-Dioleoyl-3-Dimethylammonium-Propane (DODAP), 3β-[N—(N',N'-Dimethylaminoethane)-carbamoyl]Cholesterol (DC-Cholesterol), 1,2-Dioleoyl-sn-Glycero-3-Phosphoethanolamine-N-(glutaryl) (DOPE-Glutaric acid) or a combination thereof.

6. The vesicle of claim 3, wherein the synthetic vesicle comprises a polynucleotide, polypeptide, small organic molecule, or a combination thereof.

7. The vesicle of claim 3, wherein the synthetic vesicle is loaded with cargo.

8. The synthetic vesicle of claim 3, wherein the synthetic vesicle is a liposome.

9. The vesicle of claim 3, wherein the synthetic vesicle is multilamellar.

* * * * *